United States Patent [19]

Kethley

[11] 4,269,060
[45] May 26, 1981

[54] CONTINUOUS RECORDING OF VAPOR PRESSURE

[76] Inventor: Lancelot I. Kethley, 840 York St. #8, Oakland, Calif. 94610

[21] Appl. No.: 108,212

[22] Filed: Dec. 28, 1979

[51] Int. Cl.³ .................. G01W 1/06; G01N 19/10
[52] U.S. Cl. ............................... 73/29; 73/335; 73/336; 73/337
[58] Field of Search .............. 73/29, 339 C, 336, 335, 73/337, 64.2

[56] References Cited

U.S. PATENT DOCUMENTS

| 3,461,723 | 8/1969 | Thoma | 73/335 |
| 3,688,579 | 9/1972 | Fenner | 73/337 |
| 3,797,313 | 3/1974 | Renholts | 73/337 |
| 3,937,063 | 2/1976 | Kethley | 73/29 |

FOREIGN PATENT DOCUMENTS

| 257427 | 3/1913 | Fed. Rep. of Germany | 73/336 |
| 621017 | 12/1932 | Fed. Rep. of Germany | 73/336 |
| 633161 | 7/1936 | Fed. Rep. of Germany | 73/336 |

Primary Examiner—Gerald Goldberg
Assistant Examiner—Denis E. Corr

[57] ABSTRACT

Apparatuses and methods for continuously recording the relative humidity and/or the vapor pressure of a gaseous component of a material within a gaseous mixture utilizing a relative humidity sensor having a curvature changeable with respect to changes in the relative humidity of said gaseous mixture alone or coupled to a saturation vapor pressure sensor having a linear dimension changeable with respect to changes in the saturation vapor pressure of the material and a means to contrast the linear dimension of saturation vapor pressure sensor to the span of the relative humidity sensor, the resultant value representing the actual vapor pressure of said material.

2 Claims, 3 Drawing Figures

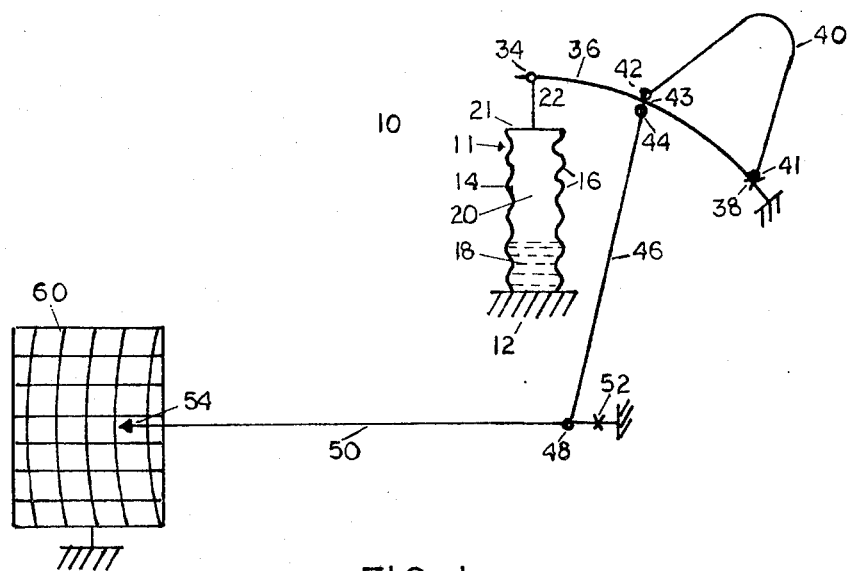
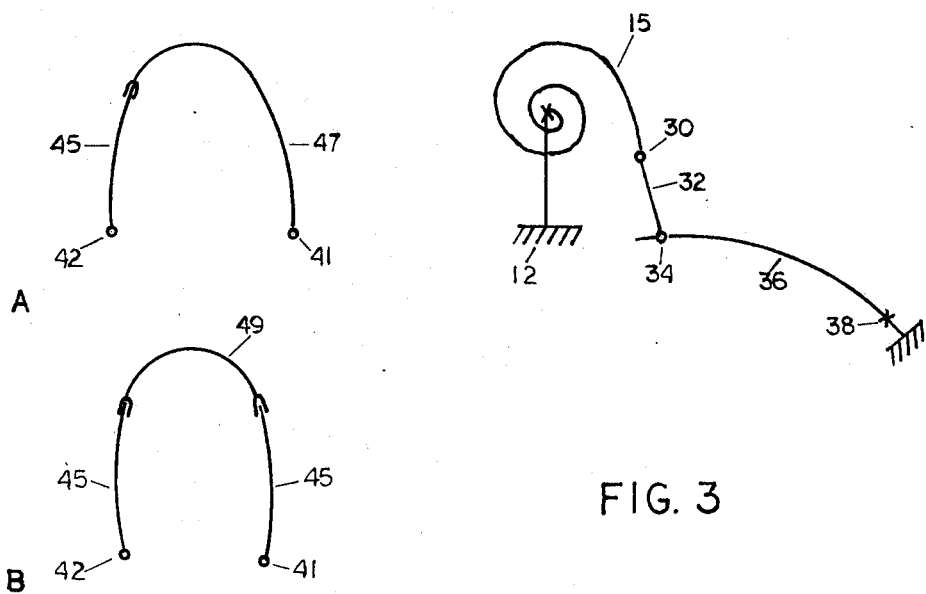
FIG. 1
FIG. 2
FIG. 3

CONTINUOUS RECORDING OF VAPOR PRESSURE

CROSS REFERENCE TO RELATED INVENTION

The present application is an improvement over the applicant's U.S. Pat. No. 3,937,063.

BRIEF SUMMARY OF THE INVENTION

The present invention is a method and apparatus for the exact measurement of the vapor pressure of a gaseous material within a gaseous mixture. The apparatus includes a saturation vapor pressure sensor formed by a closed container, such as a bourdon tube, capsule, cell or the like, or by a temperature sensor with exponential response characteristic, such as a coiled bimetall. A predetermined amount of the material being metered is disposed within the closed container such that the material exists in the vapor state over its liquid or solid state at all times. In addition, the container must flex so that increasing saturation vapor pressure increases the linear dimension of the container. A relative humidity sensor which changes its shape with the changing relative humidity, such as a strip of cane, curved and sealed on its convex side, or a strip formed from a scale of pine cone, combines with the saturation vapor pressure sensor through a means to contrast the change in length of the saturation vapor pressure sensor with the span between the arms of the relative humidity sensor.

For example, in the preferred embodiment, the end of the closed container imparts its linear expansion or contraction to a lever. The free, sweeping arm of the relative humidity sensor slides over the same lever, thus causing the length of the arm of the lever to be proportional to the relative humidity of the gaseous mixture. This is because the sweeping arm of the humidity sensor is connected to the arm of the indicator and the lever's attitude is determined by the saturation vapor pressure sensor. Hence, the indicator's position reflects the attitude of the lever subdivided by the position of the humidity sensor making the indicator's position proportional to the partial or actual vapor pressure of the metered gaseous material in the gaseous mixture in agreement with the mathematical expression that the actual vapor pressure, $P_a$, is directly proportional to the saturation vapor pressure, $P_s$, and the relative humidity, R, whence $$P_a = RP_s/100.$$

A recording chart, indicator, read out, or the like may be employed to convey the vapor pressure. Since related information, such as dew point temperature, specific humidity, and the like are readily ascertainable via mathematical or graphical methods, the chart can be scaled accordingly.

Therefore, it is an object of the present invention to provide a simple and precise apparatus and method for the measurement of the vapor pressure or partial pressure of a material in a gaseous mixture.

It is a further object of the present invention to provide sensitive, small and strong humidity sensors.

Likewise, it is a further object of the present invention to provide a useful tool for the measuring and gathering of useful meteorological data.

A further aspect of the present invention is to determine the vapor pressure of a material employing the known parameters of saturation vapor pressure and relative humidity.

Yet another objective is to provide information inferred from the vapor pressure of a component of a gaseous mixture precisely and quickly for the control of the vapor pressure or the relative humidity within such mixture.

The invention possesses other objects and advantages, especially as concerns particular features and characteristics thereof, which will become apparent as the specification continues.

BRIEF DESCRIPTION OF THE DRAWINGS

FIG. 1 is a schematic view of the apparatus.

FIG. 2 shows the installations of the humidity sensors made from pine cone scales.

FIG. 3 shows the installation of a temperature sensor in place of a saturation vapor pressure sensor.

DETAILED DESCRIPTION

The apparatus is depicted in its entirety by the numeral 10 and in FIG. 1, includes a saturation vapor pressure sensor 11, including a flexible corrugated container 14 set on surface 12. The upper end of the container 14 is provided with a plate 21, which serves to enclose container 14 and to impart linear expansion or contraction of the container to leg 22. The closed container may take the form of a bourdon tube or capsule, but, in any case, the container changes its linear dimension with respect to the change of the saturation vapor pressure of the material being metered.

Vapor pressure of the metered material is defined as the partial pressure of the gaseous phase of the metered material in a gaseous mixture. Saturation vapor pressure is defined as the pressure of the vapor phase of the metered material in contact with its liquid or solid form.

As shown by FIG. 1, the container 14 is constructed with flexible corrugations 16, which give it the characteristic of linear variation of the long axis of the container with changing saturation vapor pressure inside the container 14. The liquid component 18 of the material being metered partially fills the container 14. A space 20 is necessarily saturated by the vapor phase of the material. If the material being metered is water vapor, then the space 20 will always be saturated with water vapor.

The saturation vapor pressure of water increases pursuant to the following:

$$P_s = 10^{B-A/T}$$

where $P_s$ is the saturation vapor pressure of water, A and B are constants of the equation, values of which can be calculated, for example, from the Smithsonian Vapor Pressure Tables, and T represents the absolute temperature of the gaseous mixture.

When the temperature of the system 10 rises, a portion of the liquid phase 18 evaporates into the space 20 to maintain the condition of saturation by the vapor phase of the metered material. Therefore, container 14, by dint of its flexible corrugations 16, will expand linearly, within reasonable limits, and push leg 22 upwardly according to the increase in saturation vapor pressure of the metered material.

The relatively rigid plate 21 at the upper end of closed container 14, as aforesaid, moves linearly with the expansion and contraction of the container. Leg 22 affixes to plate 21 on one end and pivotally attaches to lever 36 on its other end through pivot 34. Leg 22 preferably attaches substantially perpendicular to lever 36, as depicted in FIG. 1. The curved lever 36 is pivotally fixed at its other end to fulcrum 38. The humidity sensor 40 is also pivotally attached to fulcrum 38 at one of its ends. Its other end 42 slides freely on lever 36. The U shaped humidity sensor 40 closes with decreasing relative humidity and stretches out with increasing relative humidity. Bar 46 attaches to the free end 42 of the humidity sensor 40 through an oval ring 43 to lever 50 by means of pivots 44 and 48. One end of lever 50 turns around fulcrum 52, its other end carries a marker 54. The length of bar 46 is adjusted so that when pivot 42 is at fulcrum 38, in case of zero relative humidity, then marker 54 is at the zero division of chart 60. The curvature of lever 36 has a radius equal to the distance between pivots 42 and 48. The span between fulcrum 38 and pivot 34 is equal to the length of the arc of lever 36 and it is determined by the span of humidity sensor 40 when the relative humidity is 100%.

In operation with the instrument properly calibrated an increase in the ambient temperature will increase the saturation vapor pressure in container 14 which in turn pushes leg 22 and turns lever 36 upwardly and vice versa. Or, in a similar situation moves the free end 30 of the temperature sensor 15 on an exponential curve pulling bar 32 and the curved lever 36 through pivot 34. The purpose of bar 32 is to allow unrestricted movements of both temperature sensor 15 and lever 36. Simultaneously, a decrease in the relative humidity will close the humidity sensor 40 proportionately and vice versa. The combined effect of the humidity sensor 40 and the saturation vapor pressure sensor 11 is recorded on the chart 60. The full extent of the movement of pivot 34 is transferred to arm 50 at pivoting point 48 when the relative humidity is 100% and the free end 42 of humidity sensor 40 is at pivoting point 34. But no movement of pivot 34 is transferred to arm 50 at pivoting point 48 when the relative humidity is 0% and the free end 42 of humidity sensor is at fulcrum 38. In between the movement of pivot 34 is subdivided or contrasted proportionately with the position of pivot 42 along lever 36.

As heretofore discussed, the material whose vapor pressure is most commonly measured is water in the earth's atmosphere. But sensors may be used to measure the vapor pressure of other materials such as ether, ammonia, and the like in other gaseous mixtures.

The actual vapor pressure, $P_a$, may be continuously recorded in any pressure units, such as millibars, millimeters or inches of mercury, pounds per square inch, and the like. Dew point temperature, specific humidity, and absolute humidity may be graphically or mathematically obtained from the value of the vapor pressure. Likewise, the chart recorder 60 may directly indicate any of these values, as desired.

To aid in calibration of the system 10 one skilled in the art may further compensate it for changes in barometric pressure by raising or lowering surface 12. This is not necessary, however, when bimetall 15 with exponential response characteristic takes the place of the saturation vapor pressure sensor 11 as depicted in FIG. 3.

In FIG. 1 the humidity sensor is shown in the form of a strip of cane. Forms, when the humidity sensor 40 is made of pine cone scales, are shown in FIG. 2. The humidity sensitive strip of pine cone scale 45 is held by an arm 47 on FIG. 2/a and two humidity sensitive strips of the same kind are connected in reverse by arm 49 on FIG. 2/b.

The foregoing description may be seen to include a method of measuring the vapor pressure of a gas or the relative humidity of a gaseous mixture. The former method incorporates the steps of measuring the linear displacement of saturation vapor pressure sensor 11 or 15, measuring the span of the humidity sensors 40, 45. These are contrasted by the use of lever 36 to determine the value of the actual vapor pressure. The latter method needs the contrasting of the span of the humidity sensor 40 or 45 against a scale.

While in the foregoing specification embodiments of the invention has been set forth in considerable detail, it will be apparent to those skilled in the art that numerous changes may be made without departing from the principles of the invention.

What is claimed is:

1. A device for continuously measuring the pressure of the vapor phase of a material within a gaseous mixture comprising:
   a. A curved elongated relative humidity sensor within the predetermined gaseous mixture, the curvature of said sensor controlling a displacement of a portion of said sensor with respect to changes in the relative humidity of said gaseous mixture;
   b. saturation vapor pressure sensor comprising a temperature sensitive element giving a displacement of a portion of said saturation vapor sensor an exponential response characteristic with respect to temperature;
   c. a displaceable component and,
   d. contrasting means acting on said displaceable component to contrast the temperature varying displacement with the relative humidity displacement, said contrasting means displacing said component as a function of the product of saturation vapor pressure and relative humidity experienced by the sensors.

2. The device of claim 1 in which said means to contrast the displacement of the saturated vapor pressure sensor with the change of curvature of the humidity sensor includes a curved lever having an arm which is variable and an attitude which changes with the displacement of said portion of the saturation vapor pressure sensor, and the length of said variable arm conveying the displacement of said portion of said saturation vapor sensor to the displaceable component changing with the curvature of the humidity sensor.

* * * * *